United States Patent
Siu et al.

(10) Patent No.: US 11,845,079 B2
(45) Date of Patent: Dec. 19, 2023

(54) INTEGRATED SILICON PLATFORM FOR ELECTRONIC BIOSENSORS

(71) Applicant: International Business Machines Corporation, Armonk, NY (US)

(72) Inventors: Vince Siu, Thornhill (CA); Sufi Zafar, Briarcliff Manor, NY (US); Benjamin Hardy Wunsch, Mt. Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 127 days.

(21) Appl. No.: 17/643,324

(22) Filed: Dec. 8, 2021

(65) Prior Publication Data
US 2023/0173484 A1     Jun. 8, 2023

(51) Int. Cl.
*G01N 33/68* (2006.01)
*G01N 21/33* (2006.01)
(Continued)

(52) U.S. Cl.
CPC ..... *B01L 3/502715* (2013.01); *B01L 3/50273* (2013.01); *B01L 3/502753* (2013.01);
(Continued)

(58) Field of Classification Search
CPC .......... B01L 3/502715; B01L 3/50273; B01L 3/502753; B01L 2200/0689;
(Continued)

(56) References Cited

U.S. PATENT DOCUMENTS

| | | |
|---|---|---|
| 9,201,041 B2 | 12/2015 | Dalton et al. |
| 10,345,317 B2 | 7/2019 | Feller et al. |

(Continued)

FOREIGN PATENT DOCUMENTS

| | | | | |
|---|---|---|---|---|
| WO | WO-2006071895 A2 | * | 7/2006 | ............ B82Y 10/00 |
| WO | 2014124365 A2 | | 8/2014 | |
| WO | 2020264204 A1 | | 12/2020 | |

OTHER PUBLICATIONS

Patent Cooperation Treaty, International Search Report and Written Opinion P202101376PCT01, International Application No. PCT EP2022/084646, dated Feb. 27, 2023, 12 pages.

(Continued)

*Primary Examiner* — Jennifer Wecker
*Assistant Examiner* — Oyeleye Alexander Alabi
(74) *Attorney, Agent, or Firm* — Kelsey M. Skodje (57) ABSTRACT

A structure, apparatus, and method are disclosed. A silicon substrate with a microfluidic system that receives a sample fluid and prepares an analyte solution received by a reservoir containing a sensing surface is electrically connected to a semiconductor device. The structure includes a component for receiving a sample fluid, a component for preparing the sample fluid, a CRISPR system for cleaving a reporter species when the sample fluid contains a target sequence, a sorting component for separating the cleaved reporter species from the sample fluid and the CRISPR products, a cavity for receiving an analyte solution containing the cleaved reporter species, and a sensing surface in the cavity. The sensing surface detects electrical signals induced by reaction events in the analyte solution.

20 Claims, 4 Drawing Sheets

(51) Int. Cl.

| | |
|---|---|
| *G01N 21/64* | (2006.01) |
| *G01N 33/52* | (2006.01) |
| *C07C 309/65* | (2006.01) |
| *C07C 309/73* | (2006.01) |
| *A01N 1/02* | (2006.01) |
| *G01N 1/40* | (2006.01) |
| *B01L 3/00* | (2006.01) |
| *C12N 15/11* | (2006.01) |
| *B82Y 5/00* | (2011.01) |

(52) U.S. Cl.
CPC ..... *C12N 15/111* (2013.01); *B01L 2200/0689* (2013.01); *B01L 2200/16* (2013.01); *B01L 2300/0663* (2013.01); *B01L 2300/087* (2013.01); *B01L 2300/0838* (2013.01); *B01L 2300/0864* (2013.01); *B01L 2400/043* (2013.01); *B01L 2400/06* (2013.01); *B82Y 5/00* (2013.01); *C12N 2310/20* (2017.05)

(58) Field of Classification Search
CPC ......... B01L 2200/16; B01L 2300/0663; B01L 2300/0838; B01L 2300/0864; B01L 2300/087; B01L 2400/043; B01L 2400/06; B01L 2300/0645; B01L 2300/0681; B01L 2200/0652; B01L 2300/0627; B01L 3/502761; C12N 15/111; C12N 2310/20; G01N 27/4145
See application file for complete search history.

(56) References Cited

U.S. PATENT DOCUMENTS

| | | | |
|---|---|---|---|
| 10,504,991 B2 | 12/2019 | Ning et al. | |
| 2013/0274113 A1* | 10/2013 | Kim | C12N 15/1048 506/1 |
| 2016/0175462 A1 | 6/2016 | Zhang et al. | |
| 2017/0136461 A1 | 5/2017 | Smith et al. | |
| 2018/0263540 A1 | 9/2018 | Zafar et al. | |
| 2018/0298445 A1 | 10/2018 | Abudayyeh et al. | |
| 2019/0107539 A1* | 4/2019 | Astier | B01L 3/502761 |
| 2019/0112643 A1 | 4/2019 | Aran et al. | |
| 2019/0321819 A1 | 10/2019 | Arango et al. | |
| 2019/0351416 A1 | 11/2019 | Culbertson | |
| 2020/0326300 A1 | 10/2020 | Aran et al. | |
| 2021/0041429 A1 | 2/2021 | Paytavi et al. | |
| 2021/0268121 A1* | 9/2021 | He | G01N 33/57488 |
| 2022/0143605 A1 | 5/2022 | Smith | |

OTHER PUBLICATIONS

Alibakhshi et al., "Picomolar Fingerprinting of Nucleic Acid Nanoparticles Using Solid-State Nanopores," ACS Nano, Oct. 24, 2017; 11(10: 9701-9710, doi: 10.102/acsnano.7b04923, 19 pgs.

Arango et al., "Electrogates for stop-and-go control of liquid flow in microfluidics," Appl. Phys. Lett. 112, 153701 (2018), https://doi.org/10/1063/1.5019469, published online Apr. 9, 2018, 6 pgs.

Bruch et al., "CRISPR/Cas13a-Powered Electrochemical Microfluidic Biosensor for Nucleic Acid Amplification-Free miRNA Diagnostics," Adv. Mater. 2019, 31, 1905311, 8 pgs.

Fozouni et al., "Amplification-free detection of SARS-CoV-2 with CRISPR-Cas13a and mobile phone microscopy," Cell 184, 323-333, Jan. 21, 2021, https://doi.org/10/1016/j.cell.2020.12.001, 21 pgs.

Gokce et al., "Self-coalescing flows in microfluidics for pulse-shaped delivery of reagents," Nature 574, 2019, 18 pgs.

Gootenberg et al., Multiplexed and portable nucleic acid detection platform with Cas13, Cas12a, and Csm6, Science, Apr. 27, 2018; 360(6387): 439-444, DOI: 10/1126/science.aaq0179, 14 pgs.

Jajian et al.. "Detection of unamplified target genes via CRISPR-Cas9 immobilized on a graphene field-effect transistor," Nature Biomedical Engineering, vol. 3, Jun. 2019, pp. 427-437.

Lau et al., "Critical review on where CRISPR meets molecular diagnostics," 2021 Prog. Biomed. Eng. 3 012001, 13 pgs.

Li et al., "CRISPR/Cas Systems Towards Next-Generation Biosensing," Trends in Biotechnology, TIBTEC 1741 pp. 1-14, 2019.

Myhrvold et al., "Field-deployable viral diagnostics using CRISPR-Cas13," https://www.researchgate.net/publication/324792029_Field-deployable_viral_diagnostics_using_CRISPR-Cas13/link/603f4085299bf1e078516cc7/download, printed Sep. 21, 2021, 7 pgs.

Prone, G., "Bipolar transistor for pH biosensors," Internship Report, Jun. 15, 2018, https://webthesis.biblio.polito.it/8487/, 34 pgs.

Smith et al., "Tailorable Electrode Capping for Microfluidic Devices," U.S. Appl. No. 17/095,538, filed Nov. 11, 2020.

Unknown, "Science explains: CRISPR diagnostics," Science Magazine, https://www.youtube.com/watch?v=22F85FOAyik, printed Sep. 21, 2021, 2 pgs.

Vangah et al., "CRISPR-Based Diagnosis of Infectious and Non-infectious Diseases," Biological Procedures Online, (2020) 22:22, https://doi.org/10.1186/s12575-020-00135-3, 15 pgs.

Xiong et al., "Local Environment Affects the Activity of Enzymes on a 3D Molecular Scaffold," ACS Nano 2020, 14, pp. 14646-14654.

Zafar et al., "A comparison between bipolar transistor and nanowire field effect transistor biosensors," Appl. Phys. Lett. 106, 063701 Feb. 2015, https://doi.org/10.1063/1.4907611, 6 pgs.

Zafar et al., "Comparison between Field Effect Transistors and Bipolar Junction Transistors as Transducers in Electrochemical Sensors," Scientific Reports, 7:41430, DOI: 10.1038/srep41430, published Jan. 30, 2017, 10 pgs.

Zafar, et al., "Silicon Nanowire Field Effect Transistor Sensors with Minimal Sensor-to-Sensor Variations and Enhanced Sensing Characteristics." ACS Nano, 2018, pp. 6577-65878.

* cited by examiner

INTEGRATED SILICON PLATFORM FOR ELECTRONIC BIOSENSORS

BACKGROUND

The present disclosure relates to electronic biosensors and, more specifically, to CRISPR-based electronic sensors integrated with semiconductor devices.

CRISPR (Clustered Regularly Interspaced Short Palindromic Repeats) systems act as molecular scissors for RNA and DNA molecules. CRISPR-based diagnostic systems rely primarily on identifying a target nucleic acid sequence associated with a given disease, which induces a collateral cleavage event of non-specific reporter molecules to produce a detectable result. For example, reporter molecules can generate fluorescent or colorimetric signals.

SUMMARY

Various embodiments are directed to a structure that includes a component for receiving a sample fluid, a component for preparing the sample fluid, a CRISPR system for cleaving a reporter species when the sample fluid contains a target sequence, and a sorting component for separating the cleaved reporter species from the sample fluid and the CRISPR products. In some embodiments, the reporter species includes a nucleic acid, a reporter ligand bound to a first end of the nucleic acid, and a bead bound to the second end of the nucleic acid. The sorting component can include a filter with pore diameters smaller than the bead. The bead can be magnetic in some embodiments. In these embodiments, the sorting component can include a magnet. In some embodiments, the sorting component includes a deterministic lateral displacement array. The structure also includes a cavity for receiving an analyte solution containing the cleaved reporter species, and a sensing surface in the cavity. The sensing surface detects electrical signals induced by reaction events in the analyte solution. The reaction events can include chemical bond formation between the reporter species and molecules coating the sensing surface. The structure also includes a semiconductor device, such as a field-effect transistor (FET) device or a bipolar junction transistor (BJT) device. electrically connected to the sensing surface. The structure can also include microfluidic channels.

Additional embodiments are directed to an apparatus that includes a semiconductor device and a silicon substrate with one or more microfluidic systems. The semiconductor device can be, for example, an FET device, a BJT device, or a nanowire device. In some embodiments, the silicon substrate has more than one of the microfluidic systems in individual wells. Each microfluidic system includes an inlet through which a sample fluid can enter, a cavity containing a reporter species, and a CRISPR system that cleaves the reporter species in the presence of a target sequence in the sample fluid. Each microfluidic system also includes a component for separating the cleaved reporter species into an analyte solution, a sensing surface electrically connected to the semiconductor device, and a reservoir in which the analyte solution contacts the sensing surface. The reservoir includes a component for inducing a reaction event in the presence of the cleaved reporter species. In some embodiments, each microfluidic system has a fluid gate controlled by embedded electrodes.

Further embodiments are directed to a method that includes providing one or more microfluidic systems on a silicon substrate. In some embodiments, the silicon substrate has more than one of the microfluidic systems in individual wells. Each microfluidic system includes a component for receiving a sample fluid, a component for preparing the sample fluid, a CRISPR system for cleaving a reporter species when the sample fluid contains a target sequence, and a sorting component for separating the cleaved reporter species from the sample fluid and the CRISPR products. In some embodiments, the reporter species includes a nucleic acid, a reporter ligand bound to a first end of the nucleic acid, and a bead bound to the second end of the nucleic acid. CRISPR reagents can be preloaded in a sample preparation cavity. The structure also includes a cavity for receiving an analyte solution containing the cleaved reporter species, and a sensing surface in the cavity. This cavity can include a reservoir in which the analyte solution contacts the sensing surface. The reservoir can include a component for inducing the reaction events in the presence of the cleaved reporter species. The sensing surface detects electrical signals induced by reaction events in the analyte solution. Each microfluidic system can include a fluid gate controlled by embedded electrodes. The method also includes providing a semiconductor device, such as a field-effect transistor (FET) device or a bipolar junction transistor (BJT) device, electrically connected to the sensing surface.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings, and will be described in detail. It should be understood, however, that the intention is not to limit the invention to the particular embodiments described. Instead, the intention is to cover all modifications, equivalents, and alternatives falling within the spirit and scope of the invention.

DETAILED DESCRIPTION

Embodiments of the present invention are generally directed to. While the present disclosure is not necessarily limited to such applications, various aspects of the disclosure may be appreciated through a discussion of various examples using this context.

Various embodiments of the present disclosure are described herein with reference to the related drawings. Alternative embodiments can be devised without departing from the scope of the present disclosure. It is noted that various connections and positional relationships (e.g., over, below, adjacent, etc.) are set forth between elements in the following description and in the drawings. These connections and/or positional relationships, unless specified otherwise, can be direct or indirect, and the present disclosure is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus. Further, the word "providing" as used herein can refer to various actions such as creating, purchasing, obtaining, synthesizing, making available, etc. or combinations thereof.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "over," "positioned on," or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements. It should be noted, the term "selective to," such as, for example, "a first element selective to a second element," means that a first element can be etched, and the second element can act as an etch stop.

As used herein, the articles "a" and "an" preceding an element or component are intended to be nonrestrictive regarding the number of instances (i.e., occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects and/or combinations of aspects as described in the specification and the claims.

Unless otherwise noted, ranges (e.g., time, concentration, temperature, etc.) indicated herein include both endpoints and all numbers between the endpoints. Unless specified otherwise, the use of a tilde (~) or terms such as "about," "substantially," "approximately," "slightly less than," and variations thereof are intended to include the degree of error associated with measurement of the particular quantity based upon the equipment available at the time of filing the application. For example, "about" can include a range of ±8% or 5%, or 2% of a given value, range of values, or endpoints of one or more ranges of values. Unless otherwise indicated, the use of terms such as these in connection with a range applies to both ends of the range (e.g., "approximately 1 g-5 g" should be interpreted as "approximately 1 g-approximately 5 g") and, in connection with a list of ranges, applies to each range in the list (e.g., "about 1 g-5 g, 5 g-10 g, etc." should be interpreted as "about 1 g-about 5 g, about 5 g-about 10 g, etc.").

It should also be understood that material compounds will be described in terms of listed elements, e.g., SiN, or SiGe. These compounds include different proportions of the elements within the compound, e.g., SiGe includes $Si_xGe_{(1-x)}$ where x is less than or equal to 1, and the like. In addition, other elements can be included in the compound and still function in accordance with the present principles. The compounds with additional elements will be referred to herein as alloys.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details. It should be noted that not all masking, patterning, and lithography processes are shown because a person of ordinary skill in the art would recognize where masking and patterning processes are utilized to form the identified layers and openings, and to perform the identified selective etching processes, as described herein.

In general, the various processes used to form a microchip that will be packaged into an IC fall into four general categories, namely, film deposition, removal/etching, semiconductor doping and patterning/lithography.

Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Another deposition technology is plasma enhanced chemical vapor deposition (PECVD), which is a process which uses the energy within the plasma to induce reactions at the wafer surface that would otherwise require higher temperatures associated with conventional CVD. Energetic ion bombardment during PECVD deposition can also improve the film's electrical and mechanical properties.

Removal/etching is any process that removes material from the wafer. Examples include etch processes (either wet or dry), chemical-mechanical planarization (CMP), and the like. One example of a removal process is ion beam etching (IBE). In general, IBE (or milling) refers to a dry plasma etch method which utilizes a remote broad beam ion/plasma source to remove substrate material by physical inert gas and/or chemical reactive gas means. Like other dry plasma etch techniques, IBE has benefits such as etch rate, anisotropy, selectivity, uniformity, aspect ratio, and minimization of substrate damage. Another example of a dry removal process is reactive ion etching (RIE). In general, RIE uses chemically reactive plasma to remove material deposited on wafers. With RIE the plasma is generated under low pressure (vacuum) by an electromagnetic field. High-energy ions from the RIE plasma attack the wafer surface and react with it to remove material.

Semiconductor doping is the modification of electrical properties by doping, for example, transistor sources and drains, generally by diffusion and/or by ion implantation. These doping processes are followed by furnace annealing or by rapid thermal annealing ("RTA"). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device.

Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and gradually the conductors, insulators and selectively doped regions are built up to form the final device.

Turning now to an overview of technologies that are more specifically relevant to aspects of the present disclosure, CRISPR (Clustered Regularly Interspaced Short Palindromic Repeats) systems act as molecular scissors for RNA and DNA molecules. CRISPR-based diagnostic systems rely primarily on identifying a target sequence associated with a disease, which induces a collateral cleavage event of non-specific reporter molecules to produce a readable fluorescent or colorimetric signals. These assays have been used to detect viruses such as dengue, zika, HPV, and COVID-19. While CRISPR-based diagnostic systems can achieve attomolar sensitivities with very high specificity, current systems' assay run times are hindered by the need for lengthy sample preparation steps and trained laboratory professionals to amplify the target sequences. For example, clinical samples such as urine, saliva, and blood require extraction of target nucleic acids by processing steps such as centrifugation, sample lysis, etc.

Embodiments of the present disclosure may overcome these and other problems. Embodiments include sample-to-answer CRISPR-based biosensors, which can use microfluidic systems integrated with semiconducting devices (e.g., bipolar junction transistors (BJTs), field-effect transistors (FETs), or nanowires) to detect target sequences present in a sample fluid. When the sample fluid contains the target sequences, the CRISPR system produces reporter molecules that can be detected electronically based on an electrical signal caused by, for example, a change in pH or a chemical bond formation. Electrical sensors can be more sensitive than optical detectors. This can allow the use of smaller sample volumes without requiring extraction and amplification of target nucleic acids.

Further, the disclosed sensors offer compatibility with silicon technology for scaling, miniaturization, and automation. For example, modules for sample processing, concentrating, and filtering samples prior to detection can be integrated with silicon technology. Silicon fabrication also allows for miniaturization and high-throughput sensing with a smaller footprint compared to optical sensors. Compartments (e.g., reservoirs, channels, etc.) of disclosed microfluidic biosensors can be optimized to allow use of low sample volumes. For example, MEMS based microfabrication techniques can be used to miniaturize and scale the platform. In further embodiments, the disclosed biosensors may be integrated in macroscale by spot-drying reagents onto paper and using wax printing to create microfluidic channels leading to a sensing surface electrically connected to the semiconductor device.

It is to be understood that the aforementioned advantages are example advantages and should not be construed as limiting. Embodiments of the present disclosure can contain all, some, or none of the aforementioned advantages while remaining within the spirit and scope of the present disclosure.

Figure 1:
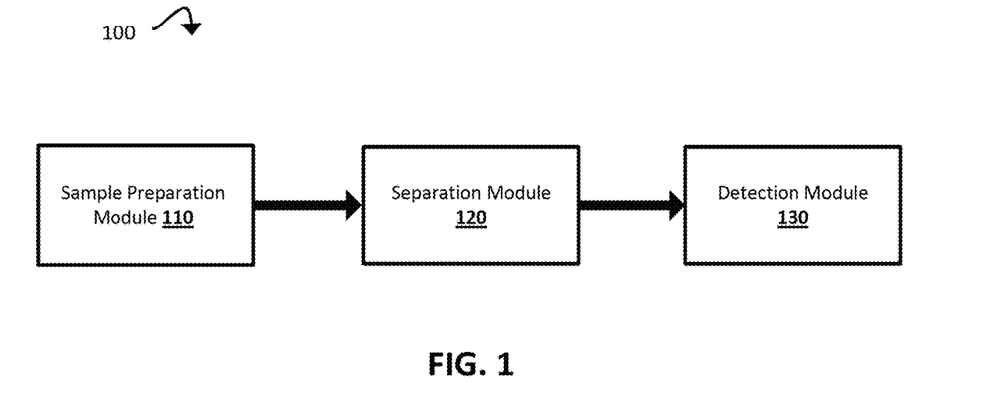
FIG. 1 is a block diagram illustrating a biosensor device, according to some embodiments of the present disclosure.

Referring now to the drawings, in which like numerals represent the same or similar elements, FIG. 1 is a block diagram illustrating biosensor 100 components, according to some embodiments of the present disclosure. The biosensor 100 can include micro- and/or macroscale fluidic systems integrated with semiconductor technology. The biosensor includes a sample processing module 110, a separation module 120, and a detection module 130. The sample processing module 110 can include sample preparation reagents, a CRISPR system, and reporter species. The separation module 120 can include components for separating collateral cleavage products to produce an analyte fluid that may contain cleaved reporter species. The detection module 130 can include a reservoir for the analyte fluid with a sensing surface electrically connected to a semiconductor device. The modules 110, 120, and 130 can include a variety of structures (e.g., channels, filters, reservoirs, electrodes, via holes, etc.), reactants (e.g., CRISPR-associated enzymes, reporter species, and other reagents), etc., which are discussed in greater detail with respect to FIGS. 2-8C.

This platform can be integrated with semiconductor technology on a macroscale by spot-drying reagents onto paper that can, for example, be part of the sample processing module 110 and using wax printing to create microfluidic channels. The biosensor 100 platform can also be integrated with semiconductor technology on a microscale (e.g., by adopting MEMS based microfabrication techniques to miniaturize and scale the platform).

Figure 2:
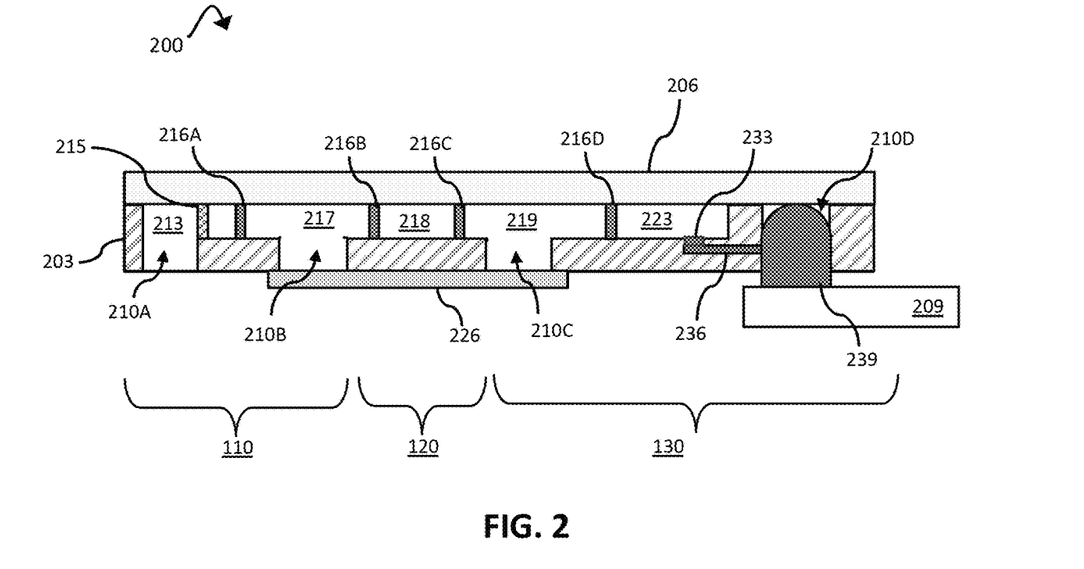
FIG. 2 is a schematic diagram illustrating a cross-sectional view of a microfluidic biosensor structure, according to some embodiments of the present disclosure.

FIG. 2 is a schematic diagram illustrating a cross-sectional view of a microfluidic biosensor structure 200, according to some embodiments of the present disclosure. Structure 200 can be a microfluidic device that includes modules 110, 120, and 130 illustrated in FIG. 1. Components of these modules 110, 120, 130 (e.g., channels, reservoirs, electrodes, conductive contacts to a semiconductor device, etc.) can be patterned and embedded into a substrate 203 such as a silicon wafer. However, in other embodiments, the substrate 203 may be made of another material, such as quartz. The material of the substrate 203 may be any suitable material or combination of materials known to one of skill in the art which supports lab-on-a-chip or other microfluidic device fabrication processes, and it may be a single layer or a plurality of sublayers.

The illustrated structure 200 can have a cover 206 layer that provides protection from the external environment. In some embodiments, at least a portion of the cover layer 206 is made of a transparent material such as glass or polymethylmethacrylate. A transparent cover layer 206 may allow more complex acceptance criteria or assays and may avoid false negative results (e.g., by repassing analyte droplets back onto a sensing surface or ensuring proper positioning and dwell time of an analyte droplet on the sensing surface).

There can be via holes 210A, 210B, 210C, and 210D (collectively 210) through the substrate 203. The vias 210 can be defined by RIE or related processes to allow loading of samples (e.g., via 210A) and reagents (e.g., vias 210B and 210C), as well as connecting electrical components (e.g., via 210D). Loading reagents can involve printing, injection, vapor phase deposition, mechanical insertion, taping, or dropping reagents into the vias 210B and 210C. The reagent-loading vias 210B and 210C can then be sealed from the backside with a substantially impermeable and mechanically robust film or membrane 226 in order to prevent loss of or damage to reagents (e.g., leakage, oxidation, etc.). Herein, "backside" refers to the side of the substrate 203 opposite the cover layer 206. Sealing can involve chemical bonding to silicon/silica at the substrate 203 surface, mechanical adhesion by crimping or clamping, thermosealing, etc. The reagents can be loaded in any phase (vapor, liquid, solid, etc.) and prevented from mixing or traveling into adjacent cavities when fluid gates 216 (see below) have been formed and closed prior to loading. In some embodiments, via holes 210 can be temporarily and selectively masked off during reagent loading to allow different sets of stages to be loaded with different reagent packages.

Additional layers/structures (not shown) may be included in biosensor 200. For example, in some embodiments, there can be interconnect layers for multi-channel devices. In another example, the biosensor structure 100/200 may include three-dimensional fluidic networks for sample and reagent distribution. There can be multiple reactor wells on a chip/substrate 203 in order to carry out simultaneous testing processes. For example, there can be an array of biosensors 100 in individual wells (see, e.g., FIGS. 8A-8C). Various samples or other fluids/solutions can be directed to the wells via channels formed on the same layer as the wells or from an overlayer formed in additional lithographic steps.

The sample processing module 110 can include a sample-loading inlet 213. The inlet 213 can include a cavity (channel and/or reservoir) for receiving a sample. The sample can be loaded through a via hole 210A open to an external environment from which the sample will be drawn. In some embodiments, the sample is loaded using a pipette, syringe, etc. In further embodiments, sample fluids may be introduced by submerging all or part of the biosensor 200 in the fluid. For example, the biosensor 200 can be mounted (e.g., embedded, adhered, suspended, etc.) in an environment such as a pond or other body of water, soil, an organism, etc. The biosensor 200 may also be incorporated into a packaging or hull of a machine or instrument for on-surface interfacing, encapsulated into a pill or intravenous mechanism, etc. In some embodiments, the biosensor 200 can be mounted on a probe station or stylus used to position the device (e.g., robotically).

The sample fluid may be immobilized in the inlet 213 cavity by a fluid gate 216A (see below) before entering further into the sample processing module 110. In some embodiments, the sample processing module 110 includes a size filter 215 positioned between the inlet 213 and the first fluid gate 216A in order to remove cell debris, large proteins, etc. from the sample fluid. Movement of fluids through the device can be facilitated by passive transport using various microfluidics techniques known in the art (e.g., capillary pumps). Active transport techniques may be used in some embodiments as well. While specific capillary pump channels/structures are not illustrated herein, it will be understood by persons of ordinary skill in the art that various channel configurations can be formed using patterning techniques discussed in greater detail above (e.g., RIE).

Each stage of the sample testing process can be isolated from upstream/downstream processes by liquid actuation valves/gates ("fluid gates") 216A, 216B, 216C, and 216D (collectively 216) that, when closed, act as barriers between structures (e.g., channels and reservoirs). In some embodiments, the biosensor 200 may include a larger or smaller number of fluid gates 216. The timing of each fluid gate's 216 opening may be preset to halt the liquid phase flow until completion of the actions in a given stage. Various techniques can be used to open the fluid gates 216 at appropriate times. For example, the fluid gates 216 may have barriers that can be dissolved by the sample fluid. This may be particularly beneficial for single-use biosensors, where fluid gates 216 that can open and close repeatedly, which can be more expensive, are not necessary.

In some embodiments, at least one of the fluid gates 216 is electronically controlled. This can allow the sample testing process to be digitally defined and activated and, optionally, guided by feedback (e.g., from sensor(s) and/or user-input instructions). The electrical signal can be a direct current (DC) voltage controlled by an external source and/or on-chip electronics. In some embodiments, the fluid gates 216 may be actuated by applying Joule heating to melt or otherwise rupture a barrier material. An electrical signal may also result in barrier removal via piezoelectricity, electrostriction, etc. In some embodiments, at least one of the fluid gates 216 can be a capillary pinning location that can be reversibly actuated by applying an electrical signal to change the surface tension of the fluid at the pinning location.

Electrodes (not shown) for actuating the fluid gates 216 can be embedded in the substrate 203 using conventional semiconductor processing techniques (e.g., damascene processes). In some embodiments, the electrodes are copper (Cu). However, any material capable of acting as an electrode can be used (e.g., aluminum (Al), titanium (Ti), tantalum (Ta), titanium nitride (TiN), tantalum nitride (TaN), tungsten (W), etc.). In some embodiments, at least a portion of each electrode can be capped by a more inert material, such as a noble metal (e.g., gold (Au), platinum (Pt), rhodium (Rh), palladium (Pd), etc.). This can improve the electrodes' compatibility with biological samples and fluids by providing protection from damage due to oxidation/corrosion, erosion, impurities, etc.

The sample processing module 110 can also include a sample preparation cavity 217. When fluid gate 216A is opened, the sample fluid can enter the sample preparation cavity 217, which can include at least one channel. The sample preparation cavity 217 may also include one or more reservoirs. Reactants for sample processing steps are present in the sample preparation cavity 217. These reactants can include sample preparation reagents, reporter species (see FIG. 3), and a CRISPR-Cas system ("CRISPR system") and can be preloaded in the cavity 217 through via hole 210B. The preloaded reactants may be substantially dry prior to entry of the sample. For example, the reagents can be at least dry/concentrated enough to delay or prevent the reagents from reacting, decomposing, etc. before being dissolved in the sample fluid.

The sample preparation reagents can include lysis reagents (e.g., for breaking apart cell components) and stabilizing reagents for preventing degradation of the nucleic acid. The sample preparation cavity 217 may include one more additional preparation components that are not illustrated herein, such as electrokinetic mixers, components for increasing sample concentration, heating, etc. These preparation components can allow samples to be input directly into the biosensor 200 without the need for additional equipment or preparation steps. However, one or more preparation steps (e.g., mixing, dissolving, etc.) may also be carried out before loading a sample in some embodiments.

The CRISPR system in the sample preparation cavity 217 includes guide RNA or DNA ("RNA/DNA") complementary to the target sequence. Binding of the target sequence to the guide RNA/DNA activates a CRISPR-associated endonuclease protein (e.g., Cas9, Cas12, Cas13, etc.). This activation induces collateral nuclease activity ("collateral cleavage"), in which non-specific reporter RNA/DNA are cut at known specific amino acid sequences. The CRISPR-system can be consistent with any appropriate CRISPR technology known in the art (e.g., SHERLOCK (Specific High Sensitivity Enzymatic Reporter UnLOCKing), DETECTR (DNA endonuclease-targeted CRISPR trans reporter), etc.). When a target sequence is present in a sample, the resulting collateral cleavage can produce cleaved reporter molecules for downstream detection. This is illustrated in FIG. 3.

Figure 3:
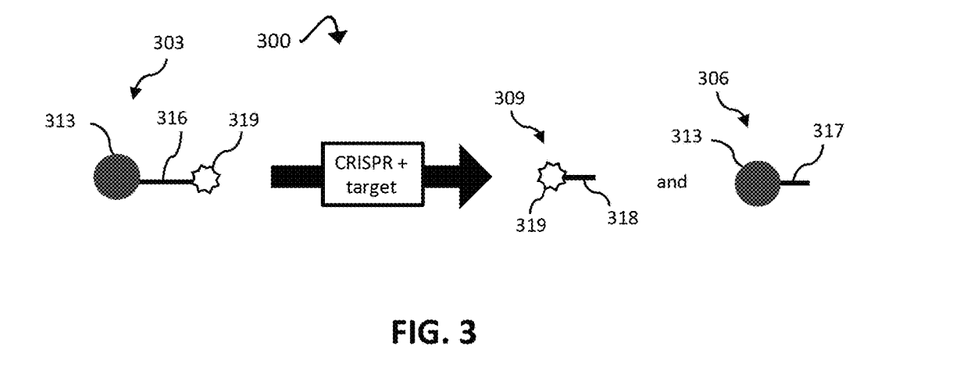
FIG. 3 is a schematic diagram illustrating a process of collateral cleavage of a reporter species, according to some embodiments of the present disclosure.

FIG. 3 is a schematic diagram illustrating a process 300 of collateral cleavage of a reporter species 303, according to some embodiments of the present disclosure. The reporter species 303 includes a bead 313 (e.g., a micro- or nanoparticle) bound to a first end of a reporter nucleic acid ("reporter sequence") 316 and a reporter ligand 319 bound to a second end of the reporter sequence 316. Examples of reporter ligands 319 can include biomolecules such as biotin, DNA fragments, enzymes, etc. In some embodiments, the reporter ligand 319 is an enzyme embedded in a DNA origami or surface-bound to a nanoparticle. Process 300 results in a cleaved bead 306 and cleaved reporter molecule ("cleaved reporter") 309. The cleaved bead 306 includes the bead 313 bound to a segment 317 of the cleaved reporter nucleic acid 316. The cleaved reporter 309 includes the remaining segment 318 of the cleaved nucleic acid 316 bound to the reporter ligand 319. Cleaved reporters 309 can be separated from the cleaved beads 306 and remaining uncleaved reporter species 303 in the separation module 120.

The separation module 120 of the structure 200 illustrated in FIG. 2 includes a separation channel 218, which can be separated from the sample processing cavity 217 by fluid gate 216B. The separation module 120 can also include additional channels and/or reservoirs, at least one sorting component for separating beads (e.g., cleaved beads 306 and uncleaved reporters 303) from cleaved reporters 309, an outlet via, etc. Examples of separation module 120 components that may be used in the separation channel 218 are discussed in greater detail with respect to FIGS. 4A-C.

Figure 4A:
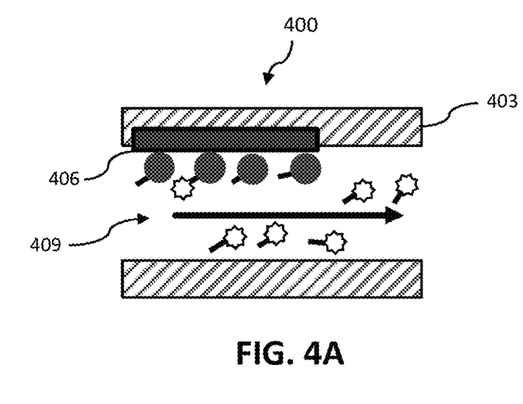
FIGS. 4A, 4B, and 4C are schematic diagrams illustrating cross-sectional views of example separation channels, according to some embodiments of the present disclosure.
Figure 4B:
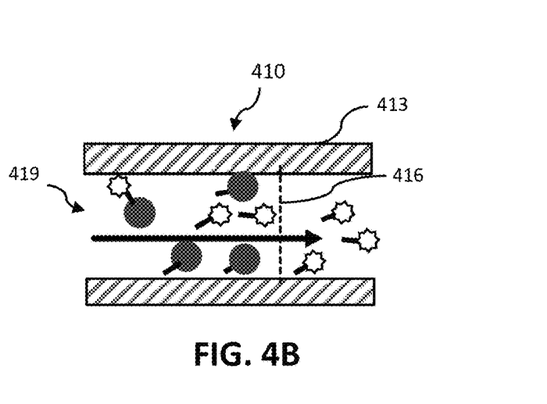
Figure 4C:
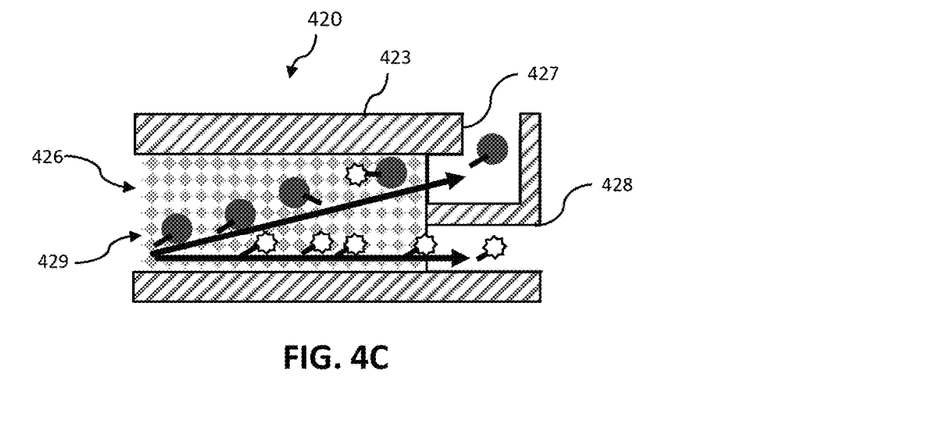

FIGS. 4A, 4B, and 4C illustrate cross-sectional diagrams 400, 410, and 420 of example separation channels 403, 413, and 423, according to some embodiments of the present disclosure. Separation channels 403, 413, and 423 are examples of separation channels that may be included in the separation module 120 (FIG. 1). In some embodiments, the separation channel 218 of biosensor 200 (FIG. 2) can be substantially similar to separation channel 403, 413, or 423. However, any appropriate separation structures/techniques can be used to separate cleaved reporters from cleaved beads and uncleaved reporters. In FIGS. 4A-C, mixtures 409, 419, and 429 contain species substantially the same as, or similar to, the reporter species 303, cleaved bead 306, and cleaved reporter 309 illustrated in FIG. 3. The flow directions of species in mixtures 409, 419, and 429 are indicated by bold arrows.

FIG. 4A illustrates a separation channel 403 with a magnetic sorting component 406. The magnetic sorting component 406 can be used to separate species in mixture 409 with magnetic beads. For example, uncleaved reporter species 303 and cleaved bead 306 can have magnetic beads 313. The magnetic sorting component 406 can attract and hold magnetic uncleaved reporter species 303 and cleaved beads 306 while allowing cleaved reporters 309 to pass through the channel 403.

FIG. 4B illustrates a separation channel 413 with a size sorting component 416. The size sorting component 416 can be a size filter with pores smaller than the bead 313 diameters of the species 303 and 306 in mixture 419. The size filter may be used to trap magnetic or non-magnetic beads. While the cleaved beads 306 and uncleaved reporters 303 are detained by the size filter, the cleaved reporters 309 can pass through separation channel 413.

FIG. 4C illustrates a separation channel 423 that sorts based on size using deterministic lateral displacement (DLD) array. Separation channel 423 can include a pillar array sorting component 426. For example, sorting structure 426 can be a microfluidic colloid separation structure based on nano- or micropillar arrays. The pillar array of sorting structure 426 is represented by a gray and white diamond pattern in FIG. 4C. This is for illustrative purposes and is not intended to precisely depict a colloid separation structure used for DLD sorting, as will be understood by those of ordinary skill. In sorting channel 423, the pillar array 426 can cause the flow path of particles above a maximum size (uncleaved reporter species 303 and cleaved beads 306) to be diverted to a waste channel, outlet, and/or reservoir 427 while smaller species (cleaved reporters 309) pass through the sorting channel 426 into a next cavity 428, which can be a component of the detection module 130. In some embodiments, there can be pillars in pillar array 426 that have sensing surfaces electrically connected to the semiconductor device 209.

It is to be understood that the separation channels shown in FIGS. 4A-C are illustrative examples, and any suitable separation mechanism known to persons of ordinary skill in the art that are not otherwise inconsistent with this disclosure are contemplated. Further, any number and combination of separation channels may be used. For example, the separation module may include both a magnetic separation channel 403 and a size sorting separation channel 413.

Turning again to FIG. 2, the fluid fraction that passes through the separation channel 218 (e.g., separation channel 403, 413, and/or 423) is referred to herein as an "analyte solution" and is tested for the presence of cleaved reporters 309 in the detection module 130. In FIG. 2, the detection module 130 of biosensor 200 includes a detector cavity 219. The analyte solution can travel through fluid gate 216C into the detector cavity 219. The detector cavity 219 can optionally include electrokinetic components (not shown) for increasing the concentration of cleaved reporter molecules, which can improve the signal-to-noise ratio during electrical signal monitoring.

The detector cavity 219 can also have reactants for inducing reaction events that can be detected electronically when cleaved reporters are present in the analyte solution. In some embodiments, the reagents can be preloaded through backside via hole 210C (see above). The reagents in the detector cavity 219 can be any materials appropriate for the type of reporter ligand on the cleaved reporters.

The detector cavity 219 can be temporarily separated from a sensing reservoir 223 by a fluid gate 216D in some embodiments. However, in other embodiments the detector cavity 219 and sensing reservoir 223 may be combined into, for example, a single reservoir. The timing of fluid gate 216D may also be adjusted based on the type of reaction events to be detected at the sensing surface 233. For example, when the reporter ligand is a DNA fragment, fluid gate 216D may be opened after a period in which isothermal amplification reactions are carried out in the detector cavity 219. Additionally, cleaved reporters with biotin reporter ligands may proceed directly from the separation channel 218 to a streptavidin-modified sensing surface 233. In another example of a detectable binding event, in which the reporter ligand is a DNA fragment, the sensing surface 233 may be coated with complementary DNA strands.

In further embodiments, the sensing surface 233 can detect the presence of the reporter ligand based on a difference in current caused by a pH and/or charge change. In these instances, the sensor materials can be materials for reacting with the ligand to induce a pH and/or charge change. For example, if the reporter ligand includes an enzyme (e.g., glucose oxidase or horseradish peroxidase), the sensor cavity 219 and/or sensor reservoir 223 can include an appropriate enzyme substrate (e.g., glucose). Binding of the substrate can result in an enzyme-catalyzed reaction that changes the pH and charge of the solution. When the reporter ligand includes DNA origami, an analyte solution pH and/or charge change may also be caused by the sugar phosphate backbone of the DNA. In another example, if the reporter ligand is a DNA fragment, the cleaved reporter can be mixed with isothermal amplification reagents. This can induce a pH and/or charge change at room temperature by amplifying the DNA fragments.

Figure 5:
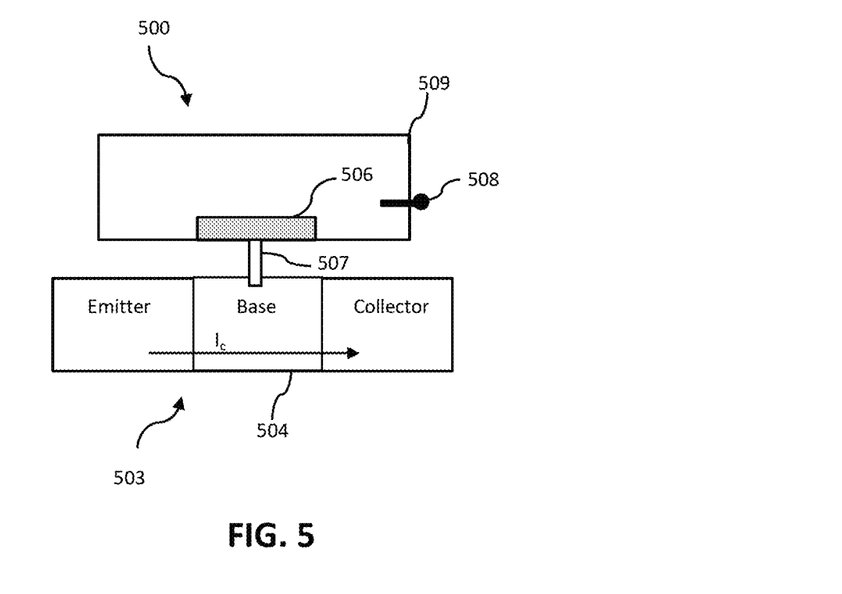
FIGS. 5 and 6 are schematic diagrams illustrating example detection module structures, according to some embodiments of the present disclosure.
Figure 6:
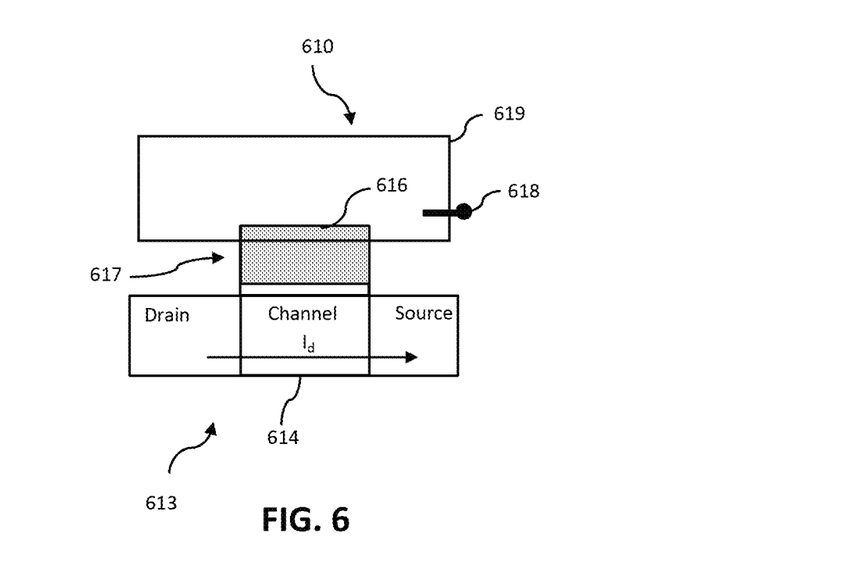

Chemical bond formation and/or pH changes on/near the sensing surface 233 can be detected by the semiconductor device 209 when a voltage is applied to the analyte solution in the sensor reservoir 223 by a reference electrode (see FIGS. 5 and 6). The sensing surface 233 can have any suitable structure for detecting electrical signals in solution. In some embodiments, the surface 233 can be a wire, a two- or three-dimensional rectangular or rounded structure, an array of pillars, etc. The sensing surface 233 can be electrically connected to semiconductor device 209 by a conductive metal trace 236 and connector 239 through a backside wiring via 210D. Examples of metals that may be used to form the conductive metal trace 236 can include silver (Ag), gold (Au), tungsten (W), nickel (Ni), titanium (Ti), molybdenum (Mo), tantalum (Ta), copper (Cu), platinum (Pt), ruthenium (Ru), iridium (Jr), rhodium (Rh), and rhenium (Re), and alloys thereof. However, any appropriate conductive material may be used (e.g., metal nitrides, silicides, etc.). The connector 239 can be a conductive metal solder ball in some embodiments. However, any appropriate connector 239 can be used, such as a metal stud. The semiconductor device 209 connected to the sensing surface 233 can be a field effect transistor (FET) or bipolar junction transistor (BJT) device (see, e.g., FIGS. 5 and 6). In some embodiments, the FET device is a silicon nanowire FET. However, any FET device suitable for microfluidic applications can be used.

In some embodiments, the detection module 130 may be coupled with optical sensing modalities (e.g., colorimetric, fluorometric, etc.) to provide additional data indicating the presence or absence of the target sequence. In these instances, reporter species that are compatible with optical sensing may be included. These can include any appropriate reporters for CRISPR with optical sensing. In some embodiments, the same reporter ligands can be detected both electrically and optically. The optical modalities may be part of an integrated on-chip optoelectronic system. The optoelectronic system may include components such as sensors, emitters, photonics, waveguides, filters, splitters, and modulators for translating optical signals into electronic signals.

FIGS. 5 and 6 are schematic diagrams illustrating example detection module structures 500 and 600, according to some embodiments of the present disclosure. The structures 500 and 600 may be components of detection module 130 and include semiconductor devices 503 and 603 (a BJT device 503 and an FET device 603), sensing surfaces 506 and 606, and sensor reservoirs 509 and 609. The sensing surfaces 506 and 606 can optionally be functionalized with biomolecules. In some embodiments, semiconductor devices 503 and 603, sensing surfaces 506 and 606, and sensor reservoirs 509 and 609 can be substantially similar to, or the same as, semiconductor device 209, sensing surface 233, and sensing reservoir 223 (FIG. 2), respectively.

The bipolar junction transistor (BJT) device 503 illustrated in FIG. 5 has a semiconductor substrate 504 with an emitter region, a base region, and collector region. An electrically conductive contact 507 can connect the base region of the substrate 504 to the sensing surface 506, which can be submerged in an analyte solution in the sensor reservoir 509. In other embodiments (not shown), the conductive contact 507 can provide a sensing surface wherein at least a portion of the contact is submerged in the sensor reservoir 509.

For example, the contact 507 can be an extended base component with a conductive surface. A first end of the extended base component (sensing surface) can be submerged in the analyte solution while a second end is connected to the base region of the substrate 504. In some embodiments, the sensing surface 506 and/or conductive contact 507 can be a titanium nitride (TiN) film. For example, an extended base component 506/507 can include a TiN film deposited over a tungsten or any other conducting wire. In some embodiments, the TiN film may be sputter deposited over the wire to a thickness of about 100 nm. The sensor reservoir 509 may be directly over the entire base region of the substrate 504, or the sensing surface 506 may connected to the base region by an extended base component/conductive contact 507.

A reference electrode 508 (e.g., an Ag/AgCl reference electrode) is also in contact with the analyte solution in the sensor reservoir 509. A sensing signal (collector current $I_c$) can be measured by varying an applied emitter voltage $V_E$ (of negative polarity for NPN BJT and of positive polarity for PNP BJT) while setting the base voltage $V_B$ and collector voltage $V_C$ to zero. However, any appropriate voltage can be applied (e.g., −2V to 2V). Reaction events induced by the presence of cleaved reporters in the sensor reservoir 509 can cause detectable changes in the collector current $I_c$ at the sensing surface 506.

Turning now to FIG. 6, the FET device 613 has a semiconductor substrate 614 with three terminals. The three terminals are known as a drain region, source region, and gate structure 617. The gate structure 617 can include a gate dielectric (white) over the channel region (between the source and drain) of the substrate 614. The gate structure 617 also includes a gate conductor (gray), which can act as a sensing surface 616 when submerged in an analyte solution in a sensor reservoir 619. In some embodiments, a greater or smaller portion of the gate conductor is submerged to provide the sensing surface 616. The sensor reservoir 619 may be directly over the entire gate conductor, or the sensing surface 616 may connected to the gate structure 617 by an extended gate conductor. In some embodiments, the sensing surface of the FET device 613 may be a metal film such as gold, silver, or copper (e.g., having a thickness between about 50 nm-150 nm).

The FET device 613 can measure drain current $I_d$ as a sensing signal by applying voltages at the drain and source regions of the substrate 614 and a reference electrode 618 in contact with the analyte solution. For example, the voltages applied to the drain, source, and reference electrode can be, respectively, about |25| mV, 0 V, and 0 V–|1 V|. However, any appropriate voltages can be applied, as will be understood by persons of ordinary skill. Reaction events induced by the presence of cleaved reporters in the sensor reservoir 619 can cause detectable changes in the drain current $I_d$ at the sensing surface 616.

Figures 7, 8A, 8B:
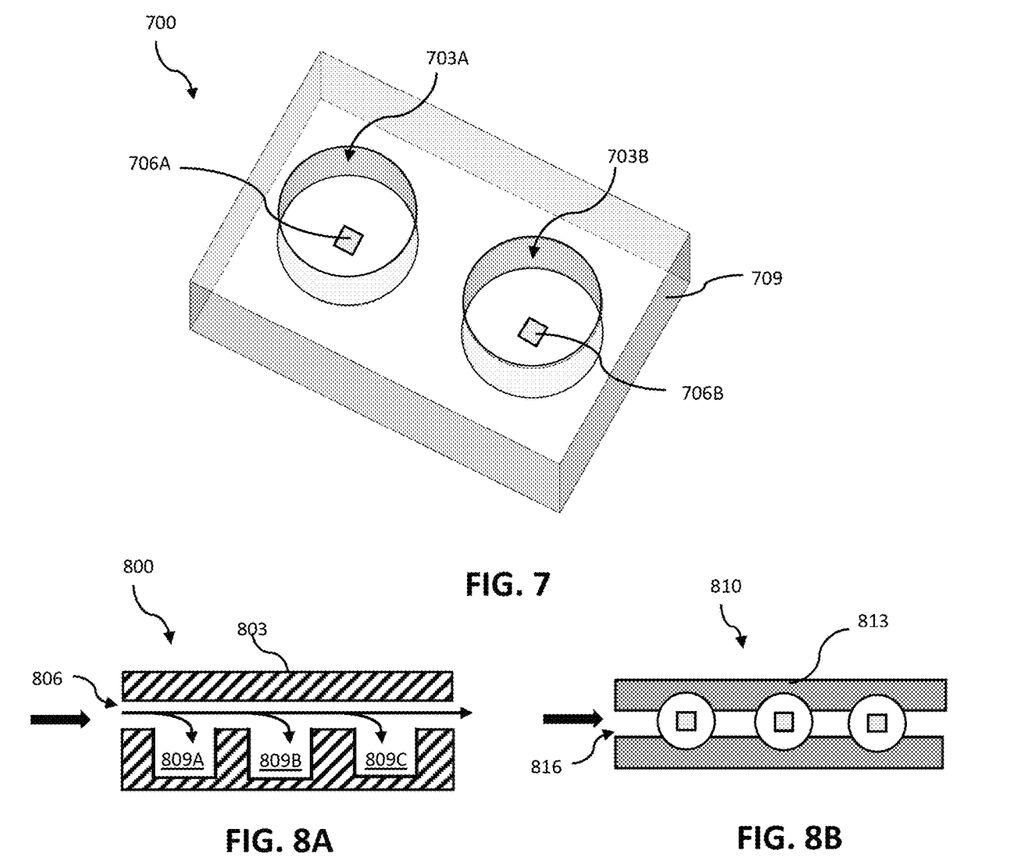
FIG. 7 is a schematic diagram illustrating a biosensor structure with more than one microfluidic system on a substrate, according to some embodiments of the present disclosure.
FIGS. 8A-8C are schematic diagrams illustrating structures with batteries of wells, according to some embodiments of the present disclosure.

FIG. 7 is a schematic diagram illustrating a biosensor structure 700 with more than one microfluidic system on a substrate, according to some embodiments of the present disclosure. The structure 700 has a substrate 709 with wells 703A and 703B (collectively 703). The wells 703 can be microscale or nanoscale structures. For example, the wells 703 may have diameters and depths of about 10 nm to 500 nm, about 500 nm-100 μm, etc. In some embodiments, such as in macroscale biosensors, the wells 703 can be larger than 100 μm. Sensing surfaces 706A and 706B (collectively 706) are embedded in wells 703A and 703B, respectively. Sensing surfaces 706 are electrically connected to semiconductor devices (see FIGS. 5 and 6). Wells 703 also include reference electrodes (not shown) for applying a voltage to analytes. While not illustrated in FIG. 7, additional components such as channels, reservoirs, metal traces, fluid gates, etc. can also be in the wells 703. For example, each well 703 can act as an individual experiment or reactor and include components such as those described with respect to biosensors 100 and 200 in FIGS. 1 and 2.

Chemical and/or biochemical changes can be monitored at sensing surfaces 706 using multiple wells 703. Each well 703 may as an isolated environment, allowing multiple independent experiments to be monitored and cross-referenced simultaneously on a single chip. In some embodiments, substrate 709 has more than two wells 703 and sensing surfaces 706 (see, e.g., FIGS. 8A-8C). Each system/well 703 may be considered a self-contained experiment. The wells 703 can optionally be back-sealed or over-sealed with an immiscible phase or sealant to encapsulate and isolate contents of each well 703.

Figure 8C:
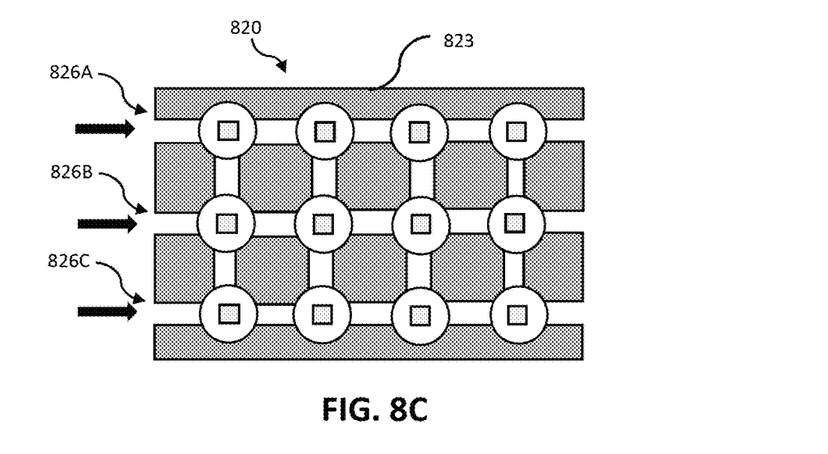

FIGS. 8A-8C are schematic diagrams illustrating structures 800, 810, and 820 with batteries of wells, according to some embodiments of the present disclosure. The structures 800, 810, and 820 each include multiple wells in/on substrates 803, 813, and 823, respectively. The wells may be substantially similar to the wells 703 illustrated in FIG. 7 and can contain biosensor components discussed in greater detail above. The flow directions of fluids (e.g., sample, analyte, etc.) entering structures 800, 810, and 820 are illustrated by block arrows.

FIG. 8A illustrates a cross-sectional view of a structure 800 having a substrate 803 with an embedded battery of wells 809A-C (collectively 809) and overlayer channel 806. Line/curved arrows represent the flow direction of fluid deposited from the channel 806 into the wells 809. While not shown in FIG. 8A, the wells 809 include sensing surfaces substantially similar to the sensing surfaces 706 illustrated in FIG. 7.

FIG. 8B illustrates a top-down view of a structure 810 having a chip substrate 813 with a linear channel 816 and battery of wells, according to some embodiments of the present disclosure. FIG. 8C illustrates a top-down view of a structure 820 having a chip substrate 823 with an area array of channels 826A-C (collectively 826) and wells. In FIG. 8C, "channels 826" refers to both horizontal (inflow direction) and vertical (perpendicular to inflow) channels. The wells (white circles) and sensing surfaces (gray squares) illustrated in FIGS. 8B and 8C can be substantially similar to the wells 703 and sensing surfaces 706 illustrated in FIG. 7.

In some embodiments, multiple systems/wells built into a chip (e.g., substrate 813 or 823) can act as sensing "pixels" for a one-time use. Multiple pixels (sensing surfaces) may be activated to allow simultaneous monitoring of multiple events, monitoring of spatially coordinated events, time-dependent monitoring of external environmental events, etc. In some embodiments, the batteries of wells can be used to form multilayer (three-dimensional) fluidic networks that can feed, in parallel, multiple sensing devices simultaneously. This can enable silicon-based microfluidic technologies such as multiplexing complex assays for healthcare with multiple biomarker targets in a single fluid sample.

The processes discussed herein, and their accompanying drawings, are not to be construed as limiting. One skilled in the art would recognize that a variety of techniques may be used that vary in conditions, components, methods, etc., which ultimately result in a biomolecule-sensing semiconductor device. In addition, the conditions can optionally be changed over the course of a process. Further, in some embodiments processes can be added, omitted, or carried out in alternate orders, while still remaining within the scope of the disclosure, as will be understood by a person of ordinary skill in the art. It should also be noted that processes can be carried out by a single entity, or by multiple entities. For example, a first entity may fabricate the biosensor device, and a second entity may test samples using the device.

The descriptions of the various embodiments of the present disclosure have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:
1. A structure, comprising:
 a component for receiving a sample fluid;
 a component for preparing the sample fluid;
 a Clustered Regularly Interspaced Short Palindromic Repeats (CRISPR) system configured for cleaving a reporter species when the sample fluid contains a target sequence;

a sorting component configured for separating the cleaved reporter species from the sample fluid and the CRISPR products; and a cavity for receiving, from the sorting component, an analyte solution containing the cleaved reporter species, wherein the cavity contains:

a component for causing a reaction event in the analyte solution, and a sensing surface, wherein the sensing surface is configured to detect electrical signals induced by the reaction events in the analyte solution, and wherein the sensing surface is connected to a semiconductor device by a conductive metal trace.

2. The structure of claim 1, wherein the reporter species comprises:

a nucleic acid;

a reporter ligand bound to a first end of the nucleic acid; and a bead bound to the second end of the nucleic acid.

3. The structure of claim 2, wherein the sorting component comprises a filter with pore diameters smaller than the bead.

4. The structure of claim 2, wherein the bead is a magnetic particle, and wherein the sorting component comprises a magnet.

5. The structure of claim 1, wherein the reaction events comprise chemical bond formation between the reporter species and molecules coating the sensing surface.

6. The structure of claim 1, further comprising microfluidic channels.

7. The structure of claim 1, wherein the semiconductor device is selected from the group consisting of a field-effect transistor (FET) device and a bipolar junction transistor (BJT) device.

8. The structure of claim 1, wherein the sorting component comprises a deterministic lateral displacement array.

9. An apparatus, comprising:

a semiconductor device; and a silicon substrate comprising one or more microfluidic systems, each microfluidic system comprising:

an inlet through which a sample fluid can enter;

a cavity containing a reporter species and a CRISPR system that cleaves the reporter species in the presence of a target sequence in the sample fluid;

a component configured for separating the cleaved reporter species into an analyte solution; and a cavity configured for receiving the analyte solution, wherein the cavity contains:

a sensing surface electrically connected to the semiconductor device by a conductive metal trace, wherein the sensing surface is configured to detect electrical signals induced by a reaction event in the analyte solution; and a reservoir in which the analyte solution contacts the sensing surface, wherein the reservoir includes a component for inducing the reaction event in the presence of the cleaved reporter species.

10. The apparatus of claim 9, wherein the semiconductor device is selected from the group consisting of a field-effect transistor (FET) device and a bipolar junction transistor (BJT) device.

11. The apparatus of claim 9, wherein the semiconductor device is a nanowire device.

12. The apparatus of claim 9, wherein the silicon substrate comprises more than one of the microfluidic systems in individual wells.

13. The apparatus of claim 9, wherein each microfluidic system further comprises a fluid gate controlled by embedded electrodes.

14. A method, comprising:

providing one or more microfluidic systems on a silicon substrate, each microfluidic system comprising:

a component for receiving a sample fluid;

a component for preparing the sample fluid;

a CRISPR system configured for cleaving a reporter species when the sample fluid contains a target sequence;

a sorting component configured for separating the cleaved reporter species from the sample fluid and the CRISPR products;

a cavity for receiving, from the sorting component, an analyte solution containing the cleaved reporter species, wherein the cavity contains:

a component for causing a reaction event in the analyte solution, and a sensing surface, wherein the sensing surface is configured to detect electrical signals induced by the reaction events in the analyte solution and wherein the sensing surface is connected to a semiconductor device by a conductive metal trace.

15. The method of claim 14, wherein each the reporter species comprises:

a nucleic acid;

a reporter ligand bound to a first end of the nucleic acid; and a bead bound to the second end of the nucleic acid.

16. The method of claim 14, wherein each microfluidic system further comprises a fluid gate controlled by embedded electrodes.

17. The method of claim 14, wherein the silicon substrate comprises more than one of the microfluidic systems in individual wells.

18. The method of claim 14, wherein the semiconductor device is selected from the group consisting of a field-effect transistor (FET) device and a bipolar junction transistor (BJT) device.

19. The method of claim 14, wherein the cavity comprises a reservoir in which the analyte solution contacts the sensing surface, and wherein the reservoir includes the component for inducing the reaction events in the presence of the cleaved reporter species.

20. The method of claim 14, wherein the providing the one or more microfluidic systems comprises preloading CRISPR reagents in a sample preparation cavity.

* * * * *